United States Patent [19]

Krumbiegel et al.

[11] Patent Number: 5,928,156
[45] Date of Patent: Jul. 27, 1999

[54] PROCESS AND DEVICE FOR THE AUTOMATIC DETECTION OF ABNORMAL BREATHING SOUNDS

[75] Inventors: Peter Krumbiegel, Leipzig; Eberhard Oberst, Dresden; Olf Herbarth, Leipzig; Hans Becker, Dresden, all of Germany

[73] Assignees: Fraunhofer-Gesellschaft Zur Forederung der Angewandten Forschung E.V.; UFZ-UmwelltforschungszenTrum Leipzig-Halle GmbH, both of Germany

[21] Appl. No.: 08/640,857
[22] PCT Filed: Oct. 28, 1994
[86] PCT No.: PCT/DE94/01282
   § 371 Date: Jun. 11, 1996
   § 102(e) Date: Jun. 11, 1996
[87] PCT Pub. No.: WO95/13019
   PCT Pub. Date: May 18, 1995

[30]    Foreign Application Priority Data

Nov. 11, 1993 [DE] Germany .............................. 43 38 466

[51] Int. Cl.$^6$ .................................................. A61B 5/02
[52] U.S. Cl. .......................... 600/529; 600/533; 600/534; 600/535; 600/536
[58] Field of Search ..................... 128/716, 671, 128/670, 773, 720, 721, 722, 723; 600/529, 533, 534, 535, 536, 484, 483, 485, 486

[56]    References Cited

U.S. PATENT DOCUMENTS 3,990,435  11/1976  Murphy ..................................... 128/716
4,428,381  1/1984   Hepp ........................................ 128/773
4,889,130  12/1989  Lee ........................................... 128/716
5,058,600  10/1991  Schechter et al. ....................... 128/716
5,165,417  11/1992  Murphy, Jr. ............................. 128/773
5,301,679  4/1994   Taylor ...................................... 128/773

FOREIGN PATENT DOCUMENTS 29 48 863 C2  7/1989  Germany .
WO 90/04945   5/1990  WIPO .

Primary Examiner—Michael Peffley
Assistant Examiner—Stephan Huang
Attorney, Agent, or Firm—Foley & Lardner

[57]    ABSTRACT

A process and a device for automatically detecting an abnormal respiratory sound permits a continuous and stress-free registration of abnormal respiratory sounds of a test person under normal life activities over a period of time. The respiratory sounds are detected, processed and evaluated in real time. From the detected frequency range, in the course of the evaluation consideration is given only to the previously determined characteristic frequencies at the position of which in the frequency spectrum of the respiratory sound of the test person an abnormal respiratory sound is to be recognized by a significant feature. The data detected at these frequency positions are compared with data which are individually determined for the test person for fulfillment of specific criteria for the occurrence of an abnormal respiratory sound, and the result of the comparison is made available as a signal. The considerable data reduction associated therewith enables the miniaturization of a corresponding device, which can then be carried by the test person over a relatively long time without restricting freedom of movement. The process is in particular suitable for the automatic monitoring of the respiratory tracts of persons suffering from and at risk from bronchitis or asthma over a relatively long period of time.

23 Claims, 1 Drawing Sheet

PROCESS AND DEVICE FOR THE AUTOMATIC DETECTION OF ABNORMAL BREATHING SOUNDS

TECHNICAL FIELD

The invention relates to a process and a device for the automatic detection and monitoring of conspicuous respiratory sounds, especially of persons suffering from and at risk from bronchitis or asthma, over a relatively long period of time.

The noninvasive, non-stressing ascertainment of experimental measured variables, by which specified noxious environmental actions on humans can be objectivized, continues to present problems, especially in human exposure research. While non-stressing methods exist for parameters such as pulse and blood pressure and even for the detoxification capacity of the liver, to date there is not yet a sufficiently simple and stress-free method which permits an objective recording of typical respiratory sounds in conjunction with likewise objectively measured emission variables. Nor is there a possibility of registering such values continuously and under normal conditions of life (in the case of children, for example, while playing in nursery school or in the open air, on the way to school, etc.) along a time coordinate, and immediately, or at a later stage, evaluating them, and possibly initiating a threshold value signal.

PRIOR ART

WO 90/04945 discloses, for example, a diagnostic process for diseases of the respiratory tract. In that process, first, preferably, the exhalation of the person to be investigated is recorded by means of a microphone. Next, the recorded respiratory sound is subjected to a spectral analysis and the result is presented in a frequency-time diagram. In this case, for example, differing colors in the diagram correspond to differing intensities. This type of presentation is intended to assist the physician in making the diagnosis, since he obtains an additional optical indication of the respiratory frequencies, from the time distribution and amplitude distribution, of which a morbid respiratory sound can be recognized.

However, it is not possible to continuously record respiratory sound during normal life activities in this way, since the vast amount of data makes evaluation and storage very costly. In this case, the treating physician must visually make the evaluation.

WO 91/03981 contains a description of a process for the automatic detection of morbid respiratory sounds. In that process, the respiratory sound of a person to be monitored is automatically detected within a cohesive frequency range in real time, processed, and evaluated. In this case, the sound waves are compared, in their amplitude and duration, with preset values which are typical of morbid respiratory sounds and, in this way, the occurrence of a morbid respiratory sound is recognized.

This process too is designed as a diagnostic process for the laboratory. It is thus not suitable in a simple manner for the detection and recording of conspicuous respiratory sounds during normal life activities. The characteristic signs, which vary from person to person, of the occurrence of morbid respiratory sounds are not taken into consideration, so that a reliable statement concerning the state of the disease is not possible in every case.

SUMMARY OF THE INVENTION

An object of the present invention is to specify a process and a device for the automatic detection of conspicuous respiratory sounds that considerably reduces the quantity of data in the course of the evaluation, with a simultaneous increase in the reliability. Accordingly, with appropriate miniaturization of the device, a continuous and stressfree registration of conspicuous respiratory sounds along a time coordinate over a period of hours or days during normal life activities is possible.

This object may be achieved by a device and a process in accordance with the invention.

The respiratory sounds of the person to be monitored are detected in real time, e.g., by a microphone, processed, and evaluated. The processing comprises, for example, amplification, noise suppression, and filtering. During the evaluation, consideration is given only to the characteristic frequency (frequencies) already determined individually for the person to be monitored prior to commencement of respiratory measurements and only at a position in the frequency spectrum of the person's respiratory sounds where a conspicuous respiratory sound can be recognized by a significant feature. This significant feature may be, for example, a particularly high amplitude at this frequency position, which would occur in the person only with a morbid eruption. Since the characteristic frequencies may be different for each individual, it is important to determine these individually in advance for each person to be monitored.

The data detected at the characteristic frequency positions is compared with data individually determined for the person to be monitored for fulfillment of one or more criteria that indicates the occurrence of a conspicuous respiratory sound. The individually determined data may be, for example, amplitude values, the exceeding or falling below of which would be a sign (criterion) of a conspicuous respiratory sound. The measured information is made available either (1) in the case of each comparison, by a signal representing the result of the comparison, or (2) only when the criterion/criteria that indicates the occurrence of a conspicuous respiratory sound is fulfilled, by a corresponding signal. The signal may be provided in analog form by a specified voltage value or, alternatively, in digital form.

The reduction of the evaluation to the characteristic frequency/frequencies leads to a considerable reduction in data and reduction in the computing expenditure, and thus to an enhanced possibility of evaluation in real time.

The comparison of the measured data with comparative values individually determined for each person, and also with the individually determined characteristic frequencies, increases the reliability of the process.

As a result of the considerable data reduction—in the minimum case, for example, data at only one characteristic frequency position is compared with only one individually determined amplitude value—the expenditure on the apparatus is also greatly reduced. Accordingly, it is possible to design an appropriate measuring device in a miniaturized construction (microsystem), which can then be carried on the body for a relatively great length of time, without restricting the freedom of movement of the person carrying it. In this way, continuous and stress-free registration of conspicuous respiratory sounds over a period of hours or days during normal life activities becomes possible.

A measuring device for carrying out the process which has just been described may consist of at least one microphone for detecting respiratory sound; at least one signal-processing unit, which includes one or more settable frequency filters to select the characteristic frequency/frequencies; an evaluating unit in which selected measured data are compared with presettable comparative values; a clock by which the temporal occurrence of conspicuous respiratory sounds can be established; a voltage supply (e.g., battery); a memory unit for the storage of the comparative values and of the comparison results; and a control unit. It is also possible to fit a plurality of microphones with a downstream signal-processing unit to the body surface of the person to be monitored (preferably in the region of the lungs). The data from the microphones may be fed to a common evaluating unit. The signal processing unit provides amplification, possibly digitization, noise suppression and filtering of the incoming signals. The characteristic frequency/frequencies may be filtered out by settable frequency filters (of analog or digital type). The comparative values and the comparison results, i.e., the signals representing the result of the comparisons or the signals which are made available only upon fulfillment of certain comparison criteria, are stored in each instance in a memory unit. Time information specified by the clock can be stored with each signal value. After the end of the measurement time (a plurality of hours or days), the information filed in the memory unit can be externally read and thus, in conjunction with the stored time information, a conclusion can be drawn as to the temporal occurrence of conspicuous respiratory sounds of the monitored person.

Using the device, characteristic sounds in the respiratory tract of the monitored persons can be recognized as typical features in the time range and frequency range, isolated from external and irrelevant sound events and detected as objective parameters. These objective parameters, which are individual to the person concerned, may be stored in time-related fashion to illustrate their value and their altering trend.

The device is preferably carried as minisensor on the person's body in low-stress fashion for a relatively long time and then externally read. In this way, it is possible to create correlations with externally measured parameters (e.g., air-hygiene data) and, if necessary, to initiate suitable medical treatments.

Overall, this invention provides a method that causes little stress to the test person and enables detection, registration and evaluation of air pollutant effects on the respiratory tract.

Such an intelligent monolithic bronchitis sensor is particularly suitable for the automatic monitoring of the respiratory tracts of persons suffering from and at risk from bronchitis or asthma; as an early warning system concerning an impending attack for groups at risk, and which can be taken along or carried on the body permanently or only in specified conditions related to weather or pollutants; for experimental epidemiological investigations on children, for example, concerning the incidence of chronic bronchitis and Asthma bronchiale in smoggy areas and in areas with various air pollutant levels; and to reduce the consumption of medicines and thus also to reduce risks and side effects associated with the medicines.

Particular embodiments of the invention are specified as follows.

In one embodiment, after each comparison, a value representing the result of the comparison is stored. This value may indicate whether the respective measured value was greater than, equal to, or less than the comparative value. Because the comparison results are stored, it is possible, after measurement over several hours or days elapses, to obtain from the stored values information concerning the frequency, the point in time, and the temporal progression of the occurrence of conspicuous respiratory sounds of the person investigated. Additionally, it is also possible to store precise time information after each comparison.

An advantageous reduction in the expenditure on memory is obtained if a determined value is stored together with time information only when the criterion (or criteria) for the occurrence of a conspicuous respiratory sound of the person to be investigated is fulfilled. It is also possible to store only the time information (as a value representing the event) so that each stored time information indicates the occurrence of a conspicuous respiratory sound at the respective point in time. The time information may represent an absolute or relative time statement, which permits a conclusion as to the absolute point in time. In this way, after the lapse of the measurement time, it may be established whether and at what time conspicuous respiratory sounds occurred.

Another embodiment of the invention involves a process that, in the event the criterion/criteria for a conspicuous respiratory sound occurs, an acoustic and/or optical and/or electrical and/or mechanical warning signal is initiated. This may comprise, for example, sound signals corresponding to an alarm signal, the flashing of a light-emitting diode, or, alternatively, voltage pulses initiating a body stimulus or mechanical (tactile) stimuli on the skin, which are emitted by an appropriate signal unit. A combination of the various possibilities may also be used. The corresponding signal should be able to be clearly perceived by the person to be investigated, in each instance, without delay, so that this person can thus be warned of an impending attack.

Since the conspicuous respiratory sounds occur only during inhalation and exhalation respectively, in a process according to the invention, the detection, processing, and evaluation of the respiratory sounds can be restricted to the inhalation and exhalation process. In this way, when using a corresponding device, the energy consumption can be reduced during the measurement time. This is achieved by a stand-by circuit, which switches the device into the so-called sleep mode for the time between two respiratory cycles.

Preferably, the respiratory frequency of the person to be monitored is in the first instance set in fixed fashion. An alteration of the respiratory frequency during the measurement (e.g. caused by increased exertions by the person) is automatically recognized on account of the characteristic sounds of the inhalation and exhalation process, and the preset value of the respiratory frequency is appropriately adapted. This may take place, for example, in such a way, that in the first instance, the detection of the respiratory sounds takes place only during fixed time windows predetermined by the preset respiratory frequency (detection only of the inhalation and exhalation process). If, for example, the sounds characteristic of exhalation end at an earlier point in time within the opened time window, then the value of the set respiratory frequency is correspondingly increased. In the same way, the value of the respiratory frequency is reduced if the inhalation process does not commence until a later point in time within the time window. In this way, the pauses between two respiratory cycles can be used optimally for energy saving.

In another preferred embodiment, the characteristic frequency (or alternatively a plurality of characteristic frequencies) to be considered in the evaluation is filtered out from the detected frequency range by appropriate settable filters, so that only the data of the frequencies of interest are fed to the evaluation.

The exceeding of an amplitude threshold value at a characteristic frequency is chosen as a criterion for the occurrence of conspicuous respiratory sounds. The amplitude threshold value (as comparative value) corresponds to a value which is individually determined for the person to be investigated prior to respiratory measurement, and exceeding that amplitude threshold value is a sign of the occurrence of a conspicuous respiratory sound.

In a process according to the invention, the values representing the result of the comparisons are stored in a form which includes information concerning the amplitude of the respective measured value at the respective frequency or, alternatively, concerning the sum of the amplitude values of determined characteristic frequencies. In both cases, information concerning the intensity of the respective attack can thus be drawn from the stored values.

The occurrence of strong disturbing sounds during the measurement time, where the disturbing sounds may impair the measurement, may be recognized by exceeding a preset amplitude threshold value. Signal processing is interrupted in this case. If the disturbing sound occurs in the pause between two respiratory cycles, detection and evaluation are not carried out in the next inhalation and exhalation process; if the disturbing sound occurs during detection and evaluation, the evaluation for that inhalation and exhalation process is interrupted and not taken into consideration.

In another embodiment, the frequency/frequencies that is/are characteristic of the person to be investigated and any individually determined data (e.g., amplitude threshold values) are obtained by a separate recording and evaluation of the respiratory sounds of the person prior to commencement of respiratory measurement. This separate recording and evaluation may take place, for example, by an auscultation by a physician.

In a further embodiment, prior to commencement of respiratory measurement, standard frequencies of the respiratory sound of the person to be investigated are first determined from the person's respiratory sound. Via these individually measured standard frequencies, the characteristic frequencies (pathofrequencies) to be expected for this person are determined from a so-called nomogram. The characteristic frequencies are taken into consideration in the process according to the invention.

In addition, the respiratory sounds may be detected at one or more positions on the body surface (e.g., at various positions in the region of the lungs) of the person to be monitored. The data detected at various positions are brought together, so that an overall evaluation and storage can take place.

In a preferred embodiment of a device according to the invention, the device has a miniaturized construction and is integrated on one or more chips. On this basis, as has already been described above, it is possible to carry the device as sensor on the body over a relatively great period of time, without restricting the patient's freedom of movement. Monitoring the respiratory sounds of the person to be investigated during normal life activities is thus possible.

BRIEF DESCRIPTION OF THE DRAWINGS

The process according to the invention and the device for carrying out the process may be explained in greater detail with reference to an illustrative embodiment in conjunction with the drawing figures.

DETAILED DESCRIPTION OF THE PREFERRED EMBODIMENT

Figure 1:
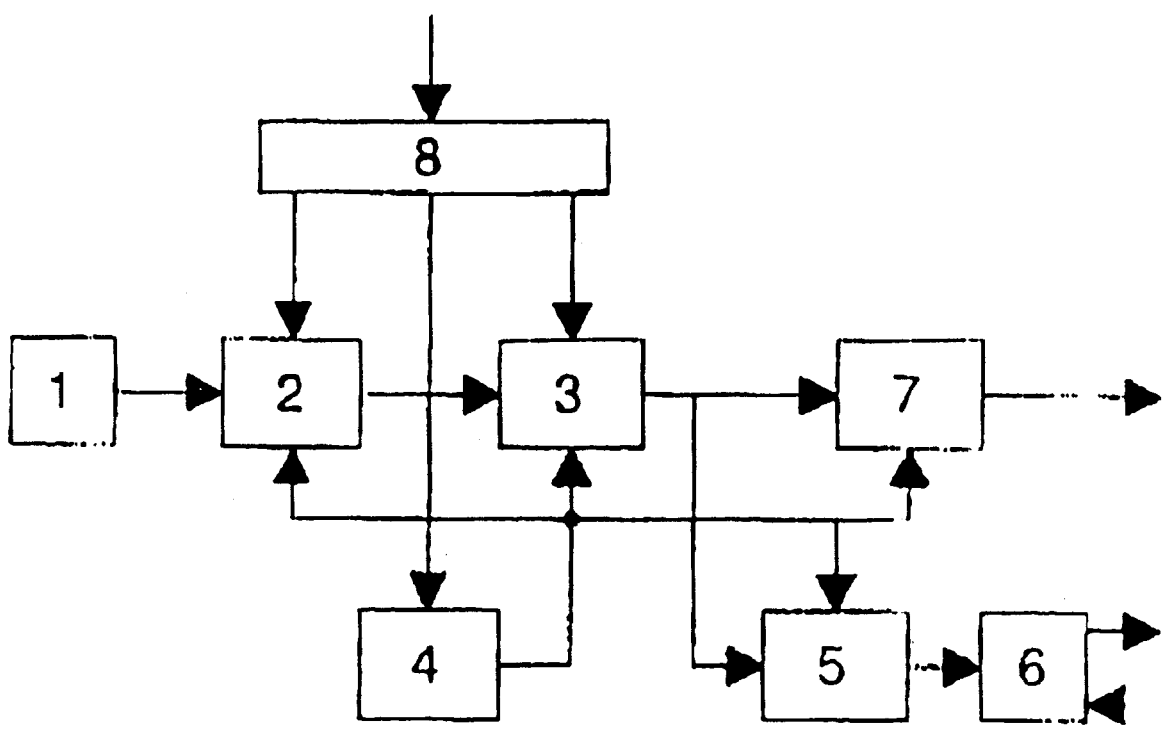
FIG. 1 shows a block circuit diagram of an illustrative embodiment of the process according to the invention.

Respiratory sounds are picked up by the microphone (1). While the respiratory frequency of the carrier is synchronized, signals emitted from the microphone (1) are passed through frequency and amplitude filters (2) to determine if they are disturbing sounds falling within the predetermined frequency range. If not, further signal processing is prevented. Only the signals falling within the frequency range and amplitude range which are of interest are passed to a feature extraction or signal processor (3). Here, the frequency signals and amplitude signals are compared with individually settable features, and these comparison results are made available in quantized form for further processing. In signal converter (7), the signals are converted, for example, into an acoustic signal so that a wearer of a bronchitis sensor may be warned in advance of an impending attack. Moreover, the signals processed in (3) are stored in a temporally correct manner in the memory (5). These signals can be stored over a relatively long period of time. Readout of the stored values can then take place in a central unit via (6), e.g., by a coupling to a telephone. The unit (4) is, in functional terms, a clock which can be set externally. The unit (4) assists the synchronization with the respiratory frequency and thus the disturbance suppression in (2), as well as the feature extraction in (3), and it serves for the imaging of the values to be stored on a continuous or discontinuous time scale. Transfer of the compact, external initialization and control information to the subsystems of the sensor system takes place via the control unit (8).

During an auscultation prior to the fitting of the sensor, the physician detects the pathological bronchial sounds of the person to be monitored. The acoustic frequencies (pathofrequencies) which are typical of pathological bronchial sounds are recorded externally. Only these characteristic frequencies and typical features determined therefrom are then input to the sensor as an internal standard and made available for signal recognition. The sensor samples only these characteristic frequencies along a time axis. As soon as interference with the predetermined features occurs, this condition is registered or stored as a signal. The clock time and possibly the time duration of this interference event are sufficient parameters to automatically monitor the respiratory tracts with respect to the pathological conditions in question.

In the case of persons, for example potentially endangered children, in whose case the prior-required internal standard of the pathological sound cannot be individually obtained, the respective pathofrequency is to be inferred from a calibration curve which has been established in advance by statistical means and with regard to size and age.

For this group of persons, the frequency spectrum of the standard respiratory sounds is individually obtained first. For these frequencies (e.g., for the exhalation sound), it is also possible to establish reliably and precisely a calibration curve of age-dependent and size-dependent standard sound frequencies. The characteristic spacing between these standard frequencies, and the expected pathofrequencies, can also be determined statistically. On this basis, it is possible to proceed with the individually measured standard frequency to a corresponding nomogram, to read from the standard frequency the pathofrequency expected for the individual, and to predetermine this as internal standard for the sensor, that is to say to set the filters to the characteristic frequencies in corresponding fashion.

The entire sensor can be designed as a microsystem. The pick-up of the sound takes place by a chip microphone (1) which can be read out in capacitive fashion. The pickup range is, for example, 20 to 2000 Hz, whereby even in the case of the pickup of the signals of interest a first filter action in the system is achieved. A further individual setting takes place by downstream programmable filters (2).

For such microsystems, the problem of energy consumption is relevant. Accordingly, only during inhalation and exhalation does the sensor pick up information and process it. In the intermediate period, a so-called sleep mode (stand-by mode) is run; the sensor prepares itself for the next measurement time.

The condition of the respiratory tracts of the monitored person is characterized by the sounds in the course of inhalation and exhalation. The breaths are clearly defined. The respiratory frequency can be set when the system is activated. This corresponds to the spacing of two successive, relatively similar groups of signals (respiratory pulses obtained from the frequency/amplitude spectrum). Altering the respiratory frequency (variation of the temporal spacing between two breaths) is automatically carried out on the basis of corresponding measurements.

A first masking-out or suppression of disturbing sounds takes place via the restriction of the observed frequency band to, for example, 20 to 2000 Hz. In addition, signal processing is barred if, between two respiratory pulses, or, during respiration, signals occur which exceed a set threshold value and would therefore render more difficult, or prevent, a perfect recognition and evaluation of the breaths.

The data obtained from the frequency/amplitude spectrum are—in certain circumstances after application of appropriate transformation algorithms (e.g., Laplace or Fourier transformations)—compared with the individually determined preset data. When individually determined set values are exceeded, the point in time of their occurrence is stored. As a result of this, registration or monitoring is restricted to few values, whereby expense on memory and power consumption of the sensor can be considerably reduced.

Readin into the memory takes place in a customary fashion: a counter counts the occupied memory locations or specifies the next memory location. Readout takes place in an externally controlled fashion via the counter which, in the case of readout, is reset or set to zero.

We claim:

1. A process for automatically detecting an abnormal respiratory sound from a patient, comprising the steps of:
    determining a target frequency range particular to the patient at which the patient's abnormal respiratory sound occurs;
    storing at least one particular distinguishing characteristic indicative of the abnormal respiratory sound occurring within the predetermined target frequency range;
    detecting respiratory sounds only in the predetermined target frequency range generated by the patient in real time;
    comparing the detected respiratory sounds falling within the predetermined target frequency range with the stored distinguishing characteristic to detect the abnormal respiratory sound from the comparison; and
    generating a signal upon detecting the abnormal respiratory sound.

2. A process according to claim 1, further comprising the steps of storing data of each comparison over a period of time, and determining frequency and temporal progression of occurrences of abnormal respiratory sounds from the stored data.

3. A process according to claim 1, further comprising the steps of storing data indicative of each occurrence of abnormal respiratory sounds upon the detection thereof over a period of time, and determining frequency and temporal progression of occurrences of abnormal respiratory sounds based on the stored data.

4. A process according to claims 1, further comprising the step of generating at least one of an acoustic, optical, electrical, and mechanical warning signal upon detecting the abnormal respiratory sound.

5. A process according to claim 1, wherein the respiratory sound detecting step takes place only during inhalation or exhalation.

6. A process according to claim 5, further comprising the steps of detecting inhalation or exhalation based on typical respiratory sounds of the patient, setting a time interval between respiratory cycles when no detection or comparison takes place, and adjusting the time interval between respiratory cycles when the respiratory cycle changes.

7. A process according to claim 1, further comprising the step of filtering the detected respiratory sounds so that only sounds within the target frequency range are compared with the stored sound distinguishing characteristic.

8. A process according to claim 1, wherein the stored distinguishing characteristic is an amplitude and wherein the amplitude of the detected sound within the target predetermined frequency range exceeding the stored amplitude indicates that the abnormal respiratory sound occurs.

9. A process according to claim 8, further comprising the steps of storing data of each comparison over a period of time, and determining frequency and temporal progression of occurrences of the abnormal respiratory sound from the stored data, wherein the data stored includes the detected amplitude and the frequency at which the amplitude is detected.

10. A process according to claim 9, further comprising the step of storing a sum of the amplitudes detected.

11. A process according to claim 1, further comprising the step of interrupting the detection of the abnormal respiratory sound when the amplitude of the detected respiratory sounds exceeds a predetermined value.

12. A process according to claim 1, wherein the step of determining the target frequency range at which the patient's abnormal respiratory sound occurs is determined by recording the patient's respiratory sound.

13. A process according to claim 1, wherein the step of determining the target frequency range at which the patient's abnormal respiratory sound occurs is obtained from a nomogram, after a nominal frequency range has been determined from the patient's respiratory sound.

14. A process according to claim 1, wherein the step of detecting the respiratory sounds generated by the patient in real time includes placing a plurality of microphones at different positions on the patient's chest.

15. A process according to claim 1, wherein the step of comparing is carried out only when the detected respiratory sounds fall within the predetermined target frequency range.

16. A device for automatically detecting an abnormal respiratory sound, comprising:
    at least one microphone adapted to be mounted to the patient's chest for detecting respiratory sounds;
    at least one signal processing unit, which includes at least one settable frequency filter for selecting a target frequency range particular to the patient at which the patient's abnormal respiratory sound occurs;
    a memory unit for storing data corresponding to at least one particular distinguishing characteristic indicative of the abnormal respiratory sound occurring within the predetermined frequency range; and
    an evaluating unit for comparing only detected respiratory sounds falling within the target frequency range with the stored data corresponding to the distinguishing characteristic, wherein the entire device is portable and adapted to be carried on the patient's chest.

17. A self-contained device according to claim 16, wherein a result of the comparison is stored in the memory unit as comparison data.

18. A self-contained device according to claim 17, further comprising a clock for tracking a time lapse and an interface for communicating the data stored in the memory unit.

19. A self-contained device according to claim 18, wherein at least the signal processing unit, the memory unit, the evaluating unit, and the clock are integrated into a plurality of semiconductor chips.

20. A self-contained device according to claim 18, wherein at least the signal processing unit, the memory unit, the evaluating unit, and the clock are integrated into a single semiconductor chip to reduce the size of the device.

21. A self-contained device according to claim 18, further comprising a signal unit for emitting at least one of an acoustic, optical, electrical, and mechanical signal upon detecting the abnormal respiratory sound.

22. A self-contained device according to claim 18, further comprising a stand-by circuit for causing the evaluating unit to compare at every other respiratory cycle to conserve energy.

23. A self-contained device according to claim 22, wherein at least the signal processing unit, the memory unit, the evaluating unit, the clock, and the stand-by circuit are integrated into a single semiconductor chip to reduce the size of the device.

* * * * *